United States Patent [19]

Whitney

[11] 4,085,138

[45] Apr. 18, 1978

[54] PROCESS FOR OPTICAL RESOLUTION OF CRUDE TRANS-1,2-CYCLOHEXANEDIAMINE

[75] Inventor: Thomas A. Whitney, Roselle, N.J.

[73] Assignee: Exxon Research & Engineering Co., Linden, N.J.

[21] Appl. No.: 711,138

[22] Filed: Aug. 3, 1976

[51] Int. Cl.$^2$ .................. C07C 87/38; C07C 87/40
[52] U.S. Cl. ................................. 260/563 R
[58] Field of Search ......................... 260/563 R

[56] References Cited

U.S. PATENT DOCUMENTS

| | | | |
|---|---|---|---|
| 3,679,746 | 7/1972 | Brake | 260/563 R |
| 3,767,707 | 10/1973 | Cleary | 260/563 R |
| 3,781,362 | 12/1973 | Blackstone | 260/563 R X |
| 3,829,490 | 8/1974 | Mueller et al. | 260/563 R X |
| 3,880,925 | 4/1975 | Langer et al. | 260/563 R |

Primary Examiner—Paul F. Shaver
Attorney, Agent, or Firm—Joseph J. Allocca; Ernest A. Gorzano

[57] ABSTRACT

Crude trans-1,2-cyclohexanediamine (DACH) contained in a mixture of amines derived as a by-product from the manufacture of 1,6-hexanediamine (HDA) or any other synthesis process crude by-product stream may be directly resolved into its optical isomers by using a mixture of tartaric acid and a second acid selected from the group consisting of $C_1$ to $C_8$ carboxylic acids and HCl, without first separating the DACH in high purity from the mixed amine component by-product stream. Alternatively, racemic DACH may be separated from a crude mixed amine component by-product stream by use of oxalic, sulfuric and/or nitric acids. This racemic product may then be optically resolved by techniques known in the art.

19 Claims, No Drawings

PROCESS FOR OPTICAL RESOLUTION OF CRUDE TRANS-1,2-CYCLOHEXANEDIAMINE

The instant invention relates to a process for the optical resolution of crude trans-1,2-cyclohexanediamine (DACH) contained in a mixture of amines derived as a by-product from the manufacture of 1,6-hexanediamine, or any other amine synthesis process, using a mixture of d- or l-tartaric acid and a second acid component selected from the group consisting of $C_1$-$C_8$ carboxylic acids and HCl. By the practice of the instant process, it is possible to directly obtain optically active (+)— or (—)—DACH in good optical yield and high optical purity without first having to separate DACH in high chemical purity from the multicomponent by-product stream in which it occurs as an incidental, difficult to isolate component. Alternatively, racemic DACH may be separated from a crude mixed multicomponent amine by-product stream by use of tartaric acid and oxalic, sulfuric and/or nitric acids as second acid components. This racemic product may then be optically resolved by techniques known in the art.

PRIOR ART

The resolution of high purity trans-DACH into its optical isomers by means of its neutral d-tartrate using water as a solvent is known in the prior art, see for example, F. M. Jager and L. Bijkerk, *Proc. Akad. Sci. of Amsterdam*, 40 (1937) p. 12 and R. G. Asperger and C. F. Liu, *Inorganic Chemistry* 4 (1965) p. 1492.

The stereospecific synthesis of trans-1,2-cyclohexanediamine (trans-DACH) is also known, e.g., F. Winternitz, M. Mousseron and R. Dennelauler, *Journal of the Chemical Society of France*, 1956, 382 and G. Swift and D. Swern., *J. Org. Chem.* 32 (1967), 511. The separation of pure trans-DACH from the cis isomer is also known, see U.S. Pat. Nos. 3,163,675 and 3,880,925. These processes, while eventually yielding the desired compounds in pure form, all suffer from the disadvantage of being multi-step process which only give optically active DACH in low yields. The most efficient process for separating cis and trans-DACH is that of U.S. Pat. No. 3,880,925 which involved the selective precipitation of trans-DACH•2HCl from methanol. To obtain optically active DACH, however, it is still necessary to subsequently resolve the pure racemic DACH so produced. Heretofore, there has been no process available for the direct optical resolution of trans-DACH from a multicomponent, mixed amine feed, by-product or output stream. For example, trans-1,2-diaminocyclohexane (trans-DACH) is just one component of a by-product stream generated in the purification of 1,6-hexanediamine (HDA) before the latter is used to manufacture Nylon 66. HDA, cis- and trans-DACH and other by-products are produced commercially by hydrogenation of adiponitrile.

THE INVENTION

It has now been discovered, quite against the expectations based upon the prior art and the best chemical intuition available, that optically active DACH is obtained in high yield and with a high degree of optical purity directly from a DACH containing by-product stream from the manufacture of HDA, without prior purification and/or separation of racemic DACH, by means of a process using a partial molar quantity of d- or l- tartaric acid in conjunction with a second acid selected from the group consisting of $C_1$ to $C_8$ mono or difunctional carboxylic acids or HCl present at a concentration equivalent to the other amines present in the mixed feedstream being treated, the reaction being run in a substantially aqueous media as solvent.

A typical mixed amine stream containing the racemic DACH of interest (which is separated into its optical antipodes by the practice of this invention), is composed of about 28% DACH, 5% 2-(aminomethyl) cyclopentyl amine and 67% HDA.

GENERAL DESCRIPTION OF THE PROCESS

Optically active (+)— or (—)— trans—DACH is separated from a mixed amine feedstream by the process of preparing a substantially aqueous solution comprising a quantity of the mixed amine feedstream, d- or l-tartaric acid, depending upon which optically active product is desired, in an amount corresponding to the mole fraction of the total DACH present in the amine mixture, a quantity of a second acid selected from the group consisting of $C_1$ to $C_7$ monofunctional carboxylic acids, $C_3$ to $C_8$ difunctional carboxylic acids, HCl and mixtures thereof in an amount equivalent to the other amines present in the crude feedstream and sufficient water or substantially aqueous medium to insure sufficient volume for the dissolution of the tartrate salts, from 1 to 10 times the volume of the mixed amine stream being preferred. Preferably the aqueous medium is pure water. The use of pure water is not critical, a substantially aqueous medium being quite acceptable. By substantially aqueous medium is meant a medium consisting of from 51 to 100% $H_2O$, preferably 75 to 100% $H_2O$, most preferably 95 to 100% $H_2O$, the balance being any material miscible with water giving a one-phase substantially aqueous solution. Mixing the above-recited components results in the production of neutral tartrate salts in a homogeneous solution. This solution is heated to a temperature below the boiling point of the solution but above room temperature, i.e., to a temperature high enough to insure complete dissolution of all components. The hot reaction mixture is seeded with a crystal of optically pure (—)—DACH•d-tartrate or (+)—DACH•l-tartrate, depending upon which optically active species is desired, and allowed to cool slowly to room temperature. If desired, the room temperature solution can be cooled to ice bath temperature. A crop of crystals separates which is recovered and added to an excess of aqueous base, the only proviso being that the base chosen liberates DACH from the tartrate salt; typically NaOH is used thereby liberating optically active DACH of about 81 to 97% or higher optical purity. The optically active DACH product is recovered by extraction of the basic mixture with an organic solvent, preferably benzene, hexane, cyclohexane, xylene, toluene, etc.

If DACH•tartrate salt does not separate immediately, the solution is concentrated by removal of water until DACH•tartrate salt crystallization does occur.

In the process of the instant invention, the use of the second acid is essential if the process is to function when using a partial molar quantity of the optically active tartaric acid. The choice of this second acid is critical, it having been discovered that $C_1$ to $C_7$ monofunctional, $C_3$ to $C_8$ α, Ω-difunctional carboxylic acids and, to a lesser extent HCl as compared to acetic acid, being the acids found to work in the process. Alternatively, racemic DACH may be separated from a mixed amine feedstream by the practice of a process similar to that described above, the only change being the substitution of oxalic, sulfuric and/or nitric acids in place of the mono- or difunctional carboxylic acids or HCl. The racemic DACH thus isolated can be treated by processes known in the prior art to yield the desired optically active DACH products. It cannot be too strongly emphasized that optical resolution of the DACH contained in the amine mixture is not achieved if a partial molar quantity of tartaric acid is used without admixture of the second acid component. Of the second acid components which are functional in the process of the instant invention, the preferred acids are formic acid, acetic acid and propanoic acid. Acetic acid is the most preferred.

The DACH containing feedstreams which are treated by the process of the instant invention can have a recoverble DACH content of anywhere from 5 to 70%, preferably, 25 to 35%. The volume of water to the volume of amine mixture used in this process ranges from 1:1 to 10:1, preferably, from about 2:1 to 3.5:1. The mole ratio of the d or l-tartaric acid to racemic DACH contained in the amine mixture can range from 0.5:1 to 2:1, preferably 1:1. The amount of the second acid component used is preferably an amount sufficient to neutralize the remaining amino groups in the amine mixture so as to afford $-NH_3^\oplus$ salts of all $-NH_2$ groups present in the amine mixture.

EXAMPLE 1

A 59.0 gram portion of a 1,2-diaminocyclohexane (DACH) containing amine mixture having a composition of about 28% DACH, 31% 2-(aminomethyl)cyclopentyl amine and 40% 1,6-hexanediamine by VPC analysis was dissolved in 177 ml of water. To the stirred solution was added 22.2g (147.7 mmoles) of d-tartaric acid which corresponds to the amount of DACH present in the amine mixture. To the solution was then added 42 ml (731 mmoles) of glacial acetic acid and the temperature of the reaction mixture increased to 60° C. A few crystals of (−)—DACH•d-tartrate were added to the hot reaction mixture and it was allowed to cool slowly to room temperature. A crop of white crystals separated which was recovered by filtration and dried, wt. 11.2g. The crystals were transferred to a liquid-liquid extractor, excess NaOH solution was added to liberate DACH from the tartrate salt and the mixture was continuously extracted with benzene for 5 hours. The benzene extract was evaporated under vacuum leaving a solid crude product which was optically active (−)—(R,R)—DACH. The crude product displayed $[\alpha]_{589}^{25} = -36.0°$ (C, 5.0, benzene) using a 10 cm cell in a Perkin-Elmer Model 141 polarimeter which corresponds to 86% optical purity. The weight of the crude product was 4.48g which corresponds to a 46% optical yield of (−)—DACH based on the amount of (−)—DACH isomer contained in the starting amine mixture and correcting the product optical purity to 100%.

EXAMPLE 2

Following the procedure detailed in Example 1, 23.41g of DACH containing amine mixture (58.6 mmoles of DACH component) 8.8g of d-tartaric acid (58.6 mmoles), 12.7 ml (293 mmoles) of formic acid and 68 ml of water were reacted. After the reaction mixture cooled to room temperature, it was further cooled to 2° C and the tartrate salt was recovered, wt. 2.5g, and was cut-back to optically active DACH. The yield was 0.9g which displayed $[\alpha]_{589}^{25} - 38.0$ (C, 5.73, benzene) which corresponds to 92.6% optical purity.

EXAMPLE 3

Following the procedure of Example 1, 23.9g of DACH containing amine mixture (60 mmoles of contained DACH), 9.0g of tartaric acid (60 mmoles), 22.2g (300 mmoles) of propanic acid and 72 ml of water were reacted. The recovered DACH tartrate weighed 4.55g and gave 1.7g of recovered (−)—DACH which displayed $[\alpha]_{589}^{25} - 39.98°$ (C, 5.4, benzene) corresponding to 97.0% optical purity.

EXAMPLE 4

Following the procedure of Example 1, 22.46g of DACH containing amine mixture (56.2 mmoles of contained DACH) 8.44g of tartaric acid (56.2 mmoles), 24.9g (283 mmoles) of butanoic acid and 67 ml of water were reacted. The recovered DACH tartrate weighed 5.2g and gave 2.1g of recovered (−)—DACH which displayed $[\alpha]_{589}^{25} - 33.57°$ (C, 5.45, benzene) corresponding to 81.4% optical purity.

EXAMPLE 5

Following the procedure of Example 1, 20.9g of DACH containing amine mixture (52.4 mmoles contained DACH), 7.86g (52.4 mmoles) tartaric acid, 31.9g of benzoic acid (261 mmoles) and 36 ml of water were reacted. The recovered DACH tartrate weighed 2.0g and gave 0.86g of recovered (−)—DACH which displayed $[\alpha]_{589}^{25} - 40.0°$ (C, 4.75, benzene) corresponding to 96.3% optical purity.

EXAMPLE 6

Following the procedure of Example 1, 22.46g of DACH containing amine mixture (56.2 mmoles of contained DACH), 8.44g of tartaric acid (56.2 mmoles), 24.2 ml of conc. HCl (281 mmoles of HCl) and 53 ml of water were reacted. No DACH tartrate separated upon cooling the reaction mixture to 2° C in the presence of a seed crystal.

The reaction mixture was concentrated on a rotary evaporator until solids dropped out. The slurry was then heated to 80° C and enough water was gradually added to redissolve all solids. The total weight of the solution was 9.17g. Upon cooling the solution to room temperature, crystals separated which were recovered, wt. 1.22g. Basic cut-back of the crystals gave 0.59g of (−)—DACH which displayed $[\alpha]_{589}^{25} - 38.6°$ (C, 4.79, benzene) corresponding to 92.9% optical purity.

Thus substitution of HCl for a carboxylic acid and using the procedure for a carboxylic acid as the second acid component does not effect optical resolution of DACH in the amine mixture. However, by modification of the carboxylic acid procedure HCl can be made to function in an inferior manner to a carboxylic acid in the instant DACH resolution process.

EXAMPLE 7

Following the procedure of Example 1, 21.15g of DACH containing amine mixture (53 mmoles contained DACH), 8.08g of d-tartaric acid, 7.5 ml of $H_2SO_4$ (135 mmoles) and 60 ml of water were reacted. A white paste formed which was diluted while hot with 100 ml of water. After cooling the solids were recovered, wt. 6.5g, and cut-back yielding 2.74g of DACH which did not display any optical activity. However, the process of this Example may be used to separate racemic DACH from the amine mixture.

EXAMPLE 8

Following the procedure of Example 1, 23.87g of DACH containing amine mixture (59.8 mmoles contained DACH) 8.97g of d-tartaric acid, 18.7 ml of 70% $HNO_3$ (299 mmoles of $HNO_3$) and 64 ml of water were reacted. No DACH•tartrate salt crystals separated.

EXAMPLE 9

A run was made according to Example 1 but no second acid component was used. No DACH•tartrate salt separated. Thus, a second acid component is necessary in the instant DACH optical resolution process.

EXAMPLE 10

Following the procedure of Example 1, 22.92g of DACH containing amine mixture (57.4 mmoles contained DACH), 8.6g (57.4 mmoles) of d-tartaric acid, 12.91g (143.4 mmoles) of oxalic acid and 169 ml of water were reacted. A white solid separated upon cooling (11.6g) which was treated with excess NaOH solution. The recovered trans-1,2-diaminocyclohexane was racemic.

EXAMPLE 11

Following the procedure of Example 1, 23.52g of DACH containing amine mixture (58.9 mmoles contained DACH), 8.88g (58.9 mmoles) of d-tartaric acid, 17.35g of succinic acid (147.1 mmoles) and 72 ml of water were reacted. A crop of crystals separated which was recovered, wt. 4.0g, and cut back with NaOH. The recovered (−)—DACH, 1.56g, displayed $[\alpha]_{25}^{589}$ − 37.75° (C, 5.56 benzene) which corresponds to 91.6% optical purity.

EXAMPLE 12

Following the procedure of Example 1, 22.4g of DACH containing amine mixture (56.3 mmoles of contained DACH), 8.44g (56.3 mmoles) of d-tartaric acid, 20.53g (140.4 mmoles) of adipic acid and 67 ml of water were reacted. A crop of white crystals separated which was recovered, wt. 4.0g, and cut back with NaOH solution. The recovered (−)—DACH, wt. 1.62g, displayed $[\alpha]_{25}^{589}$ − 39.55° (C, 5.14, benzene) which corresponds to an optical purity of 95.6%.

EXAMPLE 13

Following the procedure of Example 1, 23.06g of DACH containing amine mixture (57.7 mmoles of contained DACH), 8.7g (57.9 mmoles) of l-tartaric acid (unnatural tartaric acid), 16.4 ml (285 mmoles) of glacial acetic acid and 69 ml of water were reacted. To the hot reaction mixture was added a seed crystal of (+)—DACH•l-tartrate. Upon cooling a crop of crystals separated which was recovered, wt. 4.4g, and cut back with excess NaOH solution. The recovered (+)—DACH, wt. 1.68g, displayed $[\alpha]_{25}^{589}$ + 38.11° (C, 5.44, benzene) which corresponds to an optical purity of 91.8%. This example demonstrates that unnatural tartaric acid may be employed in the instant DACH optical resolution process to obtain the (+)—(S,S)-trans-1,2-diaminocyclohexane antipode.

What is claimed is:

1. A process for the optical resolution of racemic trans-cyclohexanediamine from a crude feedstream mixture of amines containing said racemic trans-cyclohexanediamine, said process comprising the steps of preparing a substantially aqueous solution containing a quantity of the crude amine feedstream, d- or l-tartaric acid, depending upon which optical isomer is desired, a second acid selected from the group consisting of $C_1$ to $C_7$ monocarboxylic acids, $C_3$ to $C_8$ $\alpha$, $\Omega$ difunctional carboxylic acids, HCl and mixtures thereof, and sufficient substantially aqueous medium to insure dissolution of the tartrate salts, heating the resulting mixture to a temperature sufficient to achieve dissolution of all components, seeding the hot mixture with a crystal of optically pure (+)—DACH•l-tartrate or (−)—DACH•d-tartrate, depending upon which optically active species is desired, cooling the mixture to room temperature, and separating the crystals which come out of solution.

2. The process according to claim 1 wherein the quantity of d- or l-tartaric acid added to the crude feedstream is equal to the mole fraction of the total cyclohexanediamine present in the feedstream.

3. The process according to claim 1 wherein the quantity of the second acid component added to the crude feedstream tartaric acid mixture is an amount equivalent to the other amines present in the crude feedstream.

4. The process of claim 1 wherein the second acid component is selected from the group consisting of formic, acetic and propanoic acids.

5. The process of claim 1 wherein the preferred second acid component is acetic acid.

6. The process of claim 1 wherein the mole ratio of d- or l-tartaric acid to racemic DACH contained in the crude feedstream ranges from 0.5:1 to 2:1.

7. The process according to claim 1 wherein the amount of recoverable DACH contained in the crude feedstream ranges from 5 to 70%.

8. The process according to claim 1 wherein the substantially aqueous medium used to insure dissolution of the resultant tartrate salt consists of from 51 to 100% water, the balance being any material miscible with water.

9. The process according to claim 8 wherein the water content is from 95 to 100%.

10. The process according to claim 8 wherein the substantially aqueous medium is water.

11. The process of claim 1 further characterized by the steps of cooling the total mixture in an ice bath when necessary, concentrating the solution mixture by evaporating any excess water until crystals drop out redissolving the crystals in just enough aqueous medium to achieve dissolution, cooling the resulting solution until crystals drop out.

12. A process for the separation of racemic DACH from a mixed amine feedstream comprising the steps of preparing a substantially aqueous solution containing a quantity of the mixed amine feedstream, d- or l-tartaric acid, a second acid selected from the group consisting of oxalic acid, sulfuric acid, nitric acid and mixtures thereof and sufficient substantially aqueous medium to insure dissolution of the tartrate salts, heating the resulting mixture to a temperature sufficient to achieve dissolution of all components, seeding the mixture with a crystal of DACH tartrate, cooling the mixture to room temperature, separating the crystals which come out of solution, mixing the crystals with an excess of aqueous base and separating the resultant pure racemic DACH.

13. The process according to claim 1 which further comprises mixing said crystals separated from the solution with an excess of aqueous base thereby neutralizing the tartrate salt and thus liberating pure, optically active DACH.

14. The process according to claim 13 wherein the quantity of d- or l-tartaric acid added to the crude feedstream is equal to the mole fraction of the total cyclohexanediamine present in the feedstream.

15. The process according to claim 13 wherein the quantity of the second acid component added to the crude feedstream tartaric acid mixture is an amount equivalent to the other amines present in the crude feedstream.

16. The process according to claim 13 wherein the second acid component is selected from the group consisting of formic, acetic and propanoic acids.

17. The process according to claim 13 wherein the mole ratio of d- or l-tartaric acid to racemic DACH contained in the crude feedstream ranges from 0.5:1 to 2:1.

18. The process according to claim 13 wherein the amount of recoverable DACH contained in the crude feedstream ranges from 5 to 70%.

19. The process according to claim 13 wherein the substantially aqueous medium used to insure dissolution of the resultant tartrate salt consists of from 51 to 100% water, the balance being any material miscible with water.

* * * * *